United States Patent
Park et al.

(10) Patent No.: US 6,951,547 B1
(45) Date of Patent: Oct. 4, 2005

(54) BACK IMMOBILIZING, DYNAMICALLY SELF-ADJUSTING, CUSTOMIZABLE FRAME

(76) Inventors: Dae Shik Park, 1703 Peacock La., Fullerton, CA (US) 92833; Mark Alan Latham, 16377 White Blossom Cir., Riverside, CA (US) 92503; Willard Allen Miller, 8026 Sitio Caucho, Carlsbad, CA (US) 92009

( * ) Notice: Subject to any disclaimer, the term of this patent is extended or adjusted under 35 U.S.C. 154(b) by 0 days.

(21) Appl. No.: 10/810,860

(22) Filed: Mar. 29, 2004

(51) Int. Cl.[7] .............................. A61F 5/00; A61F 5/28
(52) U.S. Cl. .................. 602/19; 128/102.1; 128/103.1
(58) Field of Search .............................. 602/19, 16, 32, 602/60, 5; 2/310–312, 338, 237, 455, 467; 128/99.1, 869, 870, 874, 101, 102.1, 103.1

(56) References Cited

U.S. PATENT DOCUMENTS

| | | | | |
|---|---|---|---|---|
| 1,100,430 A | * | 6/1914 | Haas ............................ | 602/19 |
| 1,880,946 A | * | 10/1932 | Ettinger ....................... | 602/19 |
| 1,935,859 A | * | 11/1933 | Oskar .......................... | 602/19 |
| 2,554,337 A | * | 5/1951 | Lampert ..................... | 606/237 |
| 4,202,327 A | * | 5/1980 | Glancy ........................ | 609/19 |
| 4,508,110 A | * | 4/1985 | Modglin ...................... | 602/19 |
| 4,559,933 A | * | 12/1985 | Batard et al. ................. | 602/19 |
| 5,012,798 A | * | 5/1991 | Graf et al. .................... | 602/19 |
| 5,344,391 A | * | 9/1994 | Modglin ...................... | 602/24 |
| 5,437,614 A | * | 8/1995 | Grim ........................... | 602/19 |
| 5,449,338 A | * | 9/1995 | Trudell ........................ | 602/19 |
| 5,451,200 A | * | 9/1995 | LaBella et al. ............... | 602/19 |
| 5,503,621 A | * | 4/1996 | Miller .......................... | 602/19 |
| 5,620,412 A | * | 4/1997 | Modglin ...................... | 602/24 |
| 6,099,490 A | * | 8/2000 | Turtzo .......................... | 602/19 |
| 6,102,879 A | * | 8/2000 | Christensen et al. .......... | 602/19 |
| 6,213,968 B1 | * | 4/2001 | Heinz et al. .................. | 602/19 |
| 2002/0068890 A1 | * | 6/2002 | Schwenn et al. ............. | 602/19 |

* cited by examiner

Primary Examiner—Kim M. Lewis
(74) Attorney, Agent, or Firm—Eugene Oak; Law Offices of Jane Oak & Associates, P.C.

(57) ABSTRACT

A waist support frame for a detachment type waist protecting belt to hold the vertebra region of a vertebra related patient is provided. The frame is comprised of, including but not limited to, two plastic plates. Each of the plates has a window at the center and one guiding nut on the center of the exterior side of the inner-half of the rim. The two plates are connected by two hinges, which are attached to the upper and the lower parts of the plastic plates, to form a saddle like shape that fits the contour of the waist of an individual patient dynamically.

2 Claims, 6 Drawing Sheets

BACK IMMOBILIZING, DYNAMICALLY SELF-ADJUSTING, CUSTOMIZABLE FRAME

FIELD OF THE INVENTION

The present invention relates to a waist support frame for a detachment type waist protecting belt to hold the vertebra region of a vertebra related patient, more particularly, a frame enabling self-adjustment of the waist support frame to fit to the curvatures of an individual patient's back shape dynamically.

BACKGROUND OF THE INVENTION

As is well known in the industry, the waist-protecting belt, known as an abdominal support or a pelvic girdle, is comprised of a resilient belt made of a proper material such as spandex, and a rigid back supporting plate. The role of a waist-protecting belt is to slightly compress and support the waist of a vertebra related patient's body. This prevents pain by keeping the waist in straight vertical alignment.

Adjusting the resilient belt controls pressure to the patient's back and body. However, the back supporting plate or frame, which directly touches the patient's back, is usually made of one rigid plate made of plastic or gypsum. Therefore, if the back supporting plate does not match the shape of the patient's back, it often causes undesired pain to the patient. A time consuming process of patterning the contour of a patient's back is necessary, to make the back supporting plate more effectively fit the curvature of the patient's back.

DESCRIPTION OF THE PRIOR ARTS

U.S. Pat. No. 6,322,529 to Chung illustrates a detachment type waist-protecting belt including a waist support, which fits a contour of the waist of the human body. The support is one-piece of solid material.

U.S. Pat. No. 5,399,150 Saunders illustrates a lumbosacral back support band provided with a releasable attaching back support system, which is made of one piece of composite band.

U.S. Pat. No. 5,195,948 to Hill, et al. illustrates a back support device comprised of a belt structure designed to fit substantially around the waist of a user. An inflatable air bladder is attached inside the belt structure so that it is positioned adjacent to the lower back when the back support device is worn.

U.S. Pat. No. 5,127,897 to Roller illustrates a therapeutic back support device including a plastic back support plate, which is coupled to a human body to forwardly direct the plate.

U.S. Pat. No. 4,752,982 to Jones, et al. illustrates an adjustable back support apparatus with an anchor assembly to adjustably connect the main support, and a cushion assembly connected to the main support base assembly.

U.S. Pat. No. 3,889,664 to Heuser, et al. illustrates two torso belt members, joined together with a jack screw connector, intended to apply traction to the user between the pair of belts.

None of the prior arts introduces a back support plate, the shape of which is easily adjustable with the adjustment of a single strap.

SUMMARY OF THE INVENTION

A waist support frame for a detachment type waist-protecting belt to hold the vertebra region of a vertebra related patient is provided. The waist support frame is comprised of, including but not limited to two plastic plates, each of which has a window at the center and one guiding nut on the center of the exterior side of the inner-half of the rim, connected by two hinges, which are attached to the upper and the lower parts of the plastic plates, to form a saddle like shape that fits the contour of the waist of an individual patient dynamically. The support frame of the current invention is applicable to conventional waist protecting belts. The support frame eliminates a time consuming process of patterning the shape of a patient's back. When wearing this hinged support frame, patients with abnormal body structures, such as, a narrow chest with big hips and abdomen or a big chest with narrow hips, will feel more comfortable than patients accustomed to other one piece solid plastic/plaster plates by adjusting the curvature of the supporting frame dynamically by themselves.

BRIEF DESCRITION OF THE DRAWINGS

Figure 2:
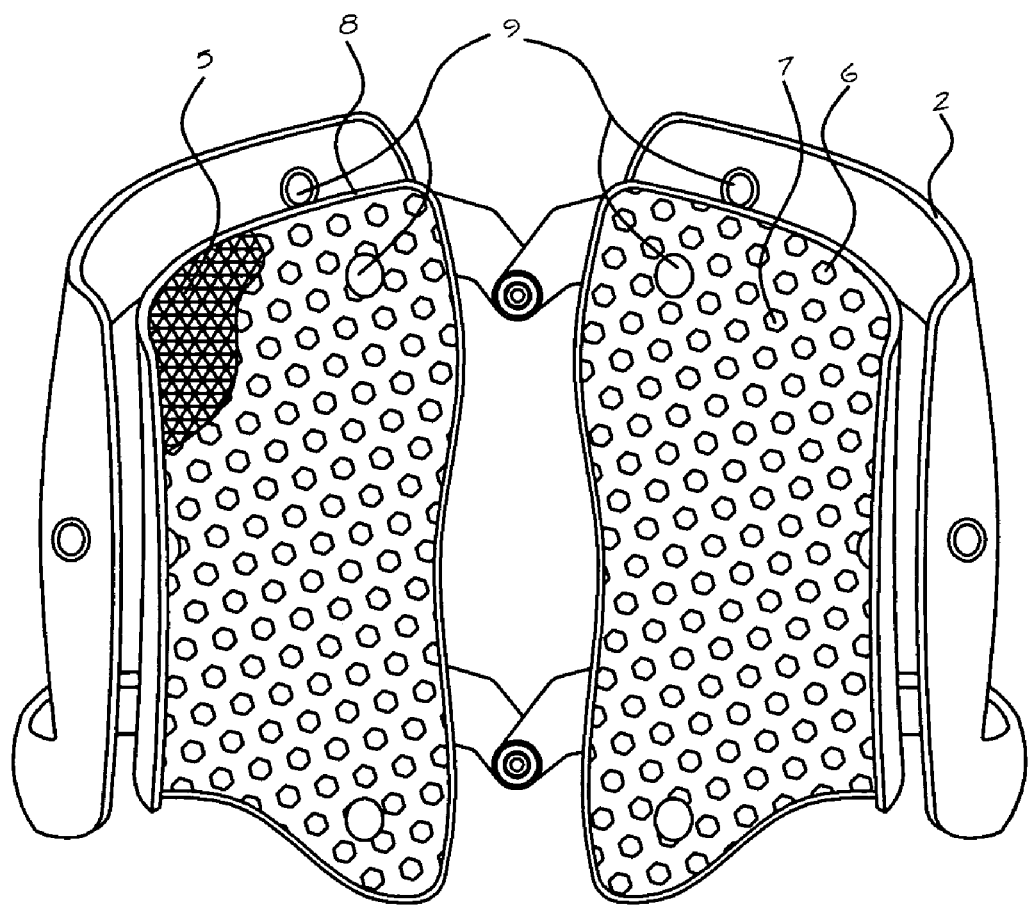
FIG. 2 is an expanded perspective view of the back supporting frame from inside of the frame.
Figure 3A:
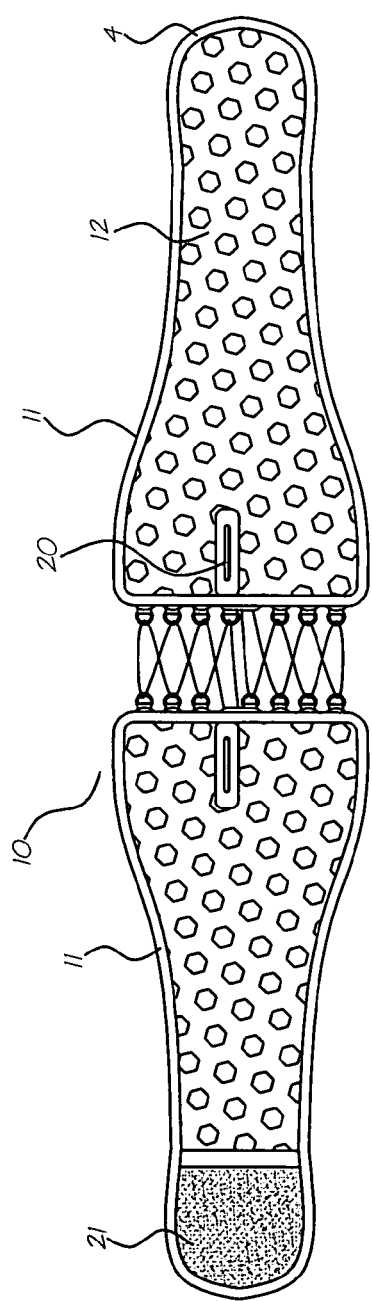
Figure 3C:
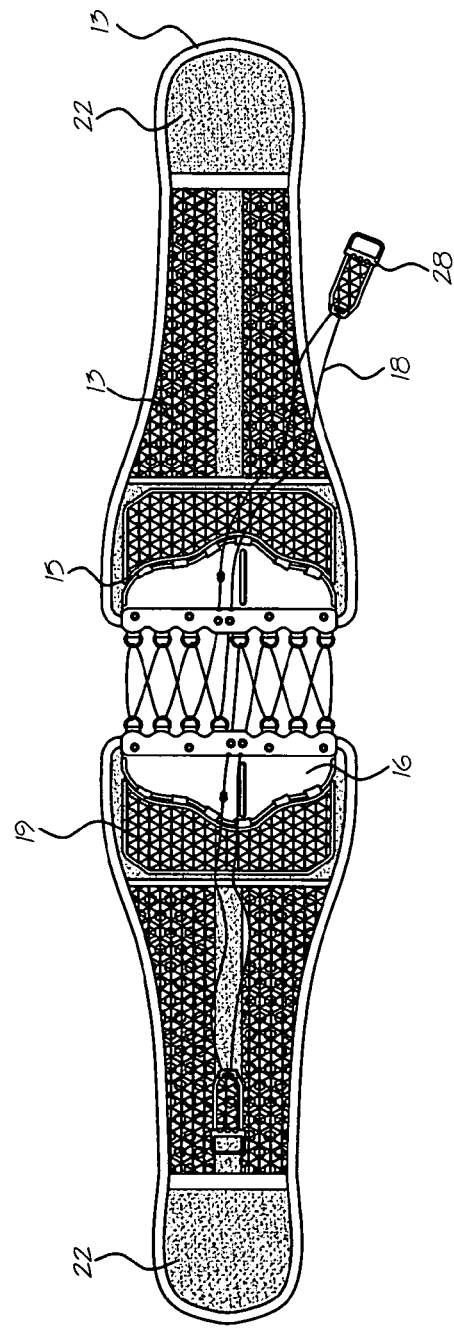
Figure 3B:
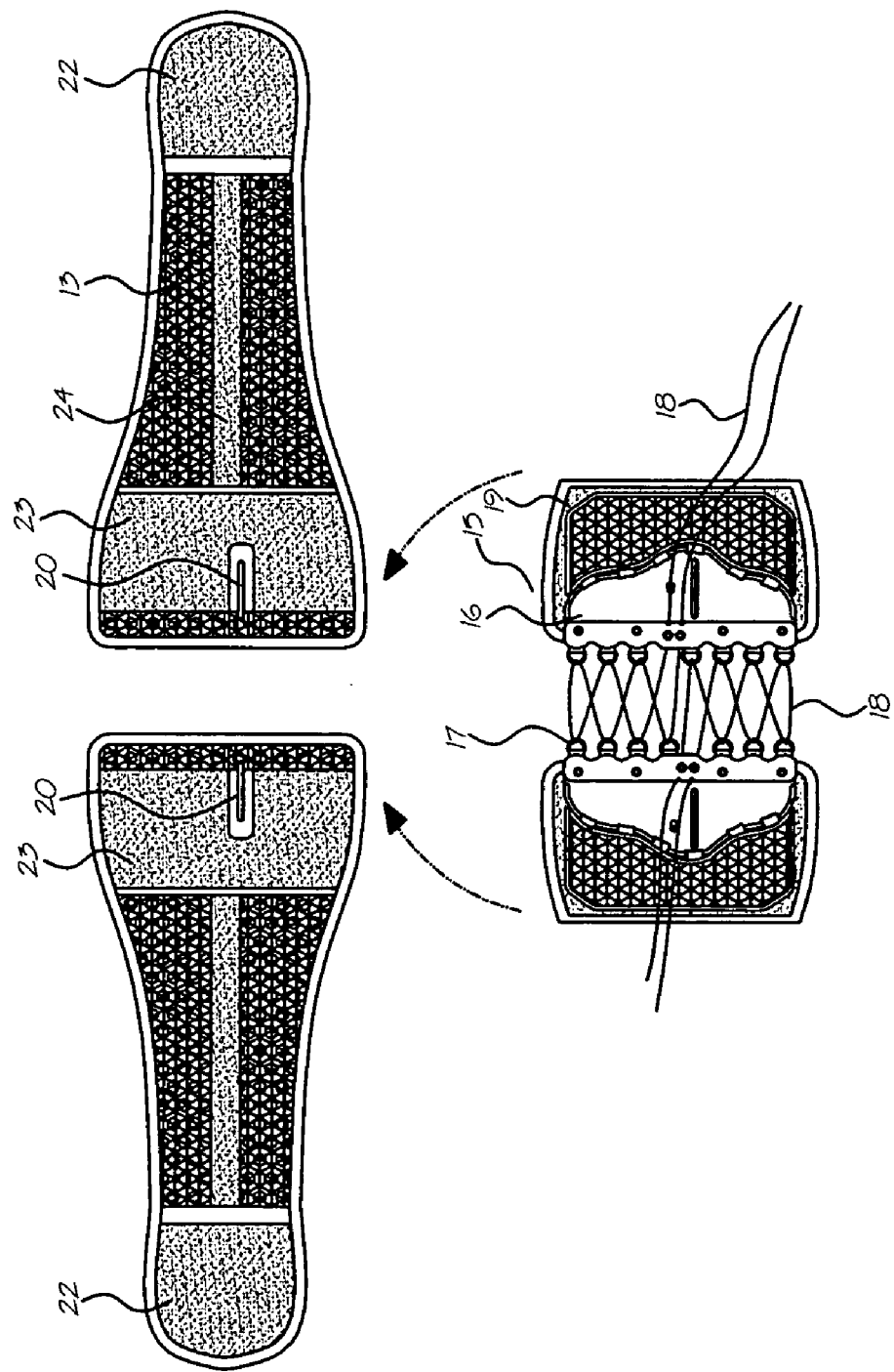

FIG. 3-*a* is a view of the back supporting belt of prior art for mounting the back supporting frame of FIG. 2 from inside of the belt.

FIG. 3-*b* shows the bands and the fastening connectors of the supporting band of prior art.

FIG. 3-*c* is a view of the back supporting belt of prior art for mounting the back supporting frame of FIG. 2 from outside of the belt.

Figure 4:
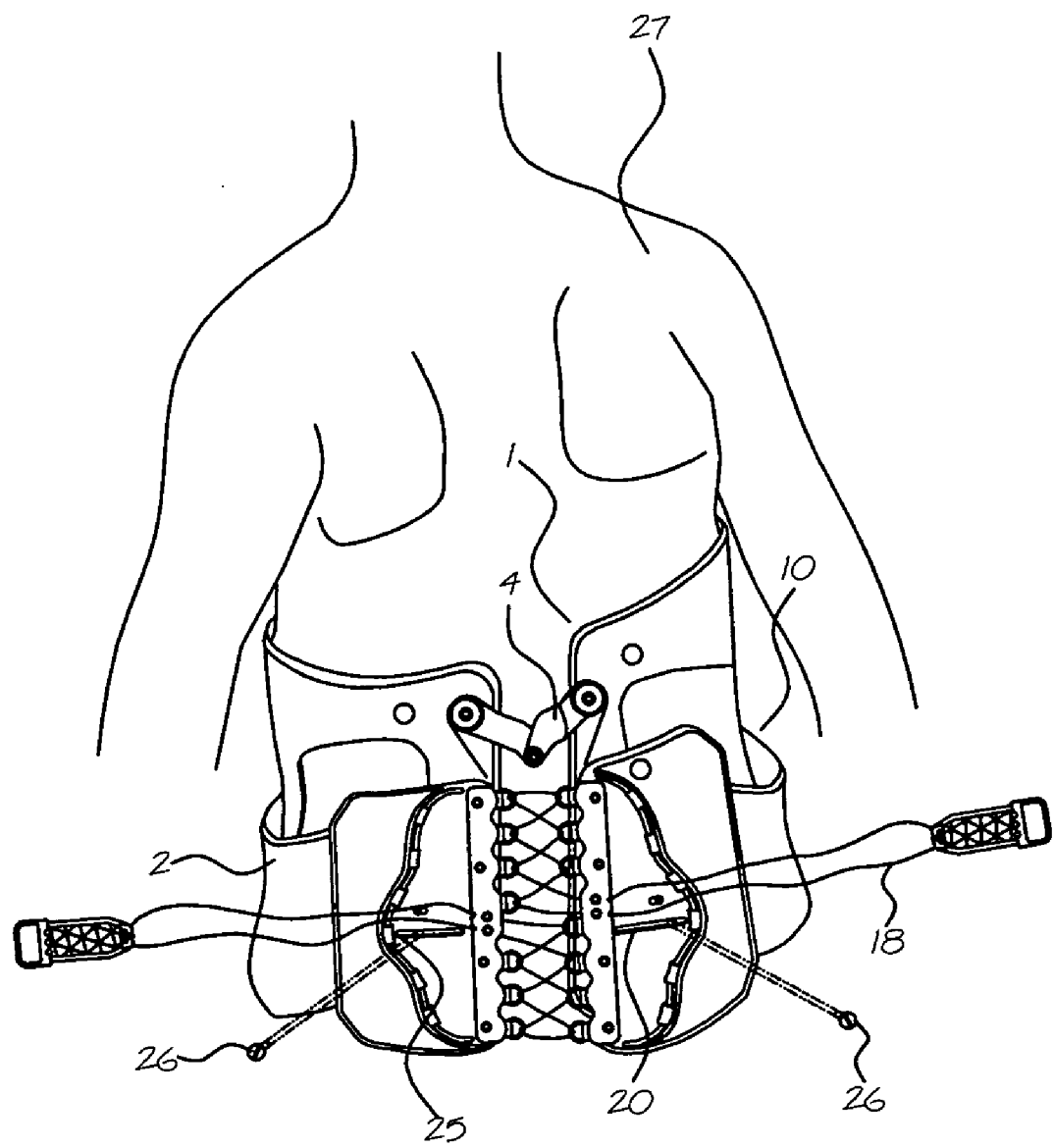

FIG. 4 is a schematic diagram showing how to attach the back support frame to the back supporting belt and how to put the back support frame on the patient's back.

Figure 5:
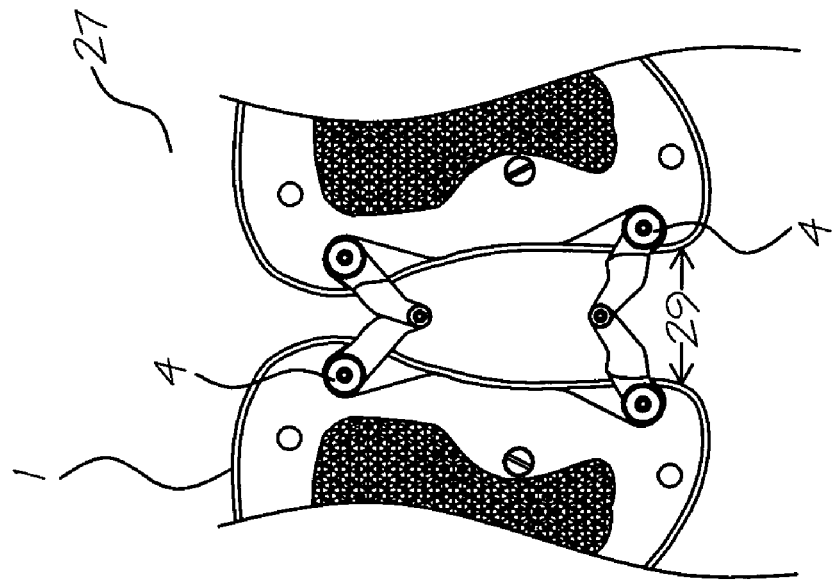
Figure 5:
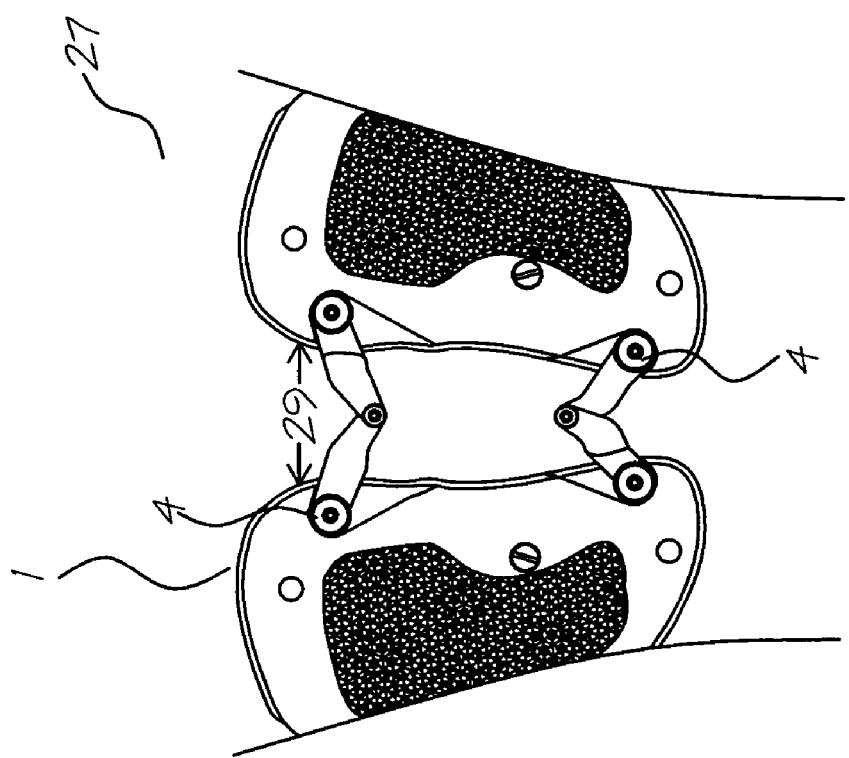

FIG. 5 is the schematic drawings showing the back supporting frames (1) worn by patients with varied waist contours.

DETAILED DERCRIPTION OF THE PREFERRED EMBODIMENT

Figure 1:
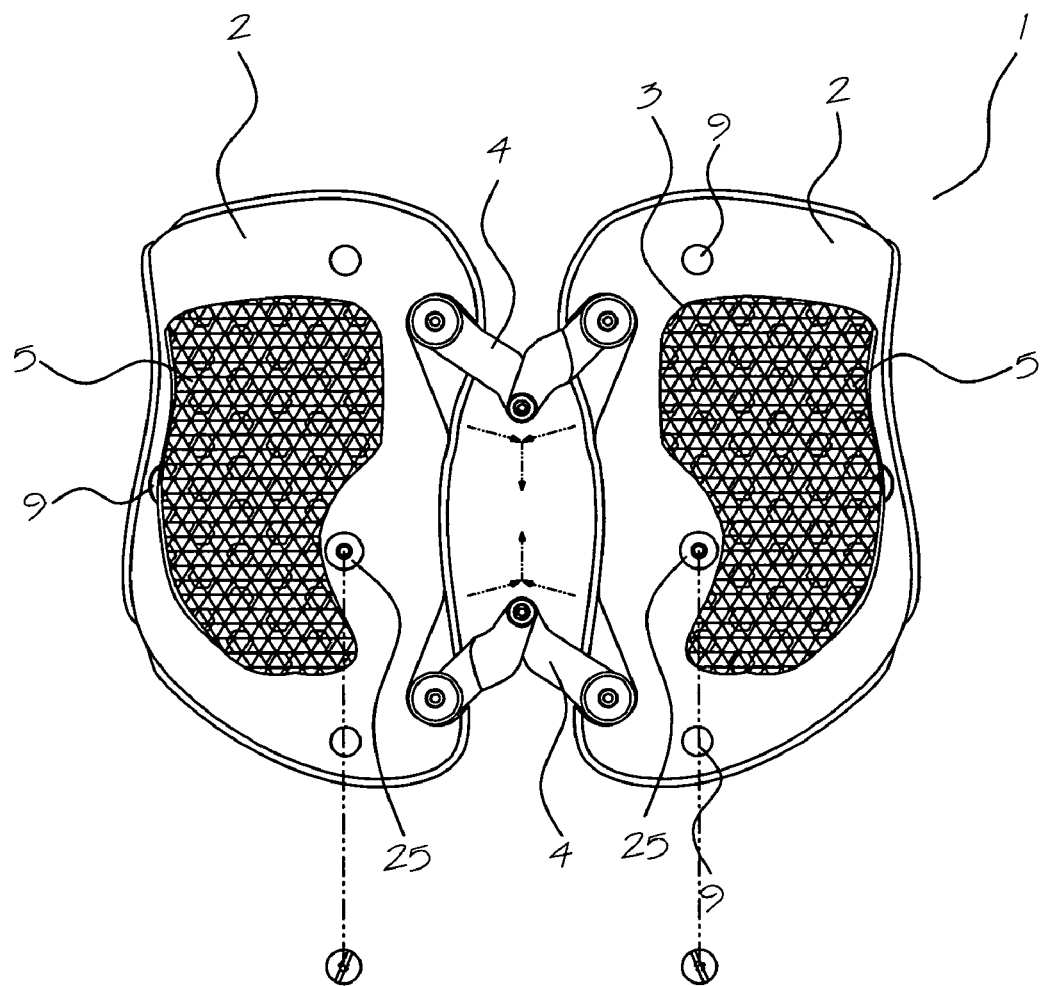
FIG. 1 is a front view of the back supporting frame looking from the out side of the frame when it is stretched.

FIG. 1 is a front view of the back supporting frame (1) of the current invention looking from the outside of the frame when it is stretched. And FIG. 2 is an expanded perspective view of the back supporting frame from inside of the frame. The supporting frame (1) is comprised of, including but not limited to, two plastic plates (2), each of which has a window (3) at the center and one guiding nut (25) on the center of the exterior side of the inner-half of the rim, connected by two hinges (4), which are attached to the upper and lower parts of the plastic plates, to form a saddle like shape that fits the contour of the waist of an individual patient.

Two sheets of plastic mesh (5) line the inside of each plastic plate (2). Two sheets of a soft elastic layer (6), with pluralities of holes (7) for air ventilation are threaded to the inside of each of the plastic mesh sheets, providing a cushion layer between the waist of the individual patient and the two plastic plates (2) attached to the frame (1). The perimeters (8) of the plastic mesh (5) and the elastic layer (6) are threaded to become one piece. The mesh (5) and the elastic layer (6) are attached to the back support plates (2) via snap buttons (9).

FIG. 3-*a* to FIG. 3-*c* are inside and outside views of a back supporting belt (10) of prior art. The belt (10) is comprised of two bands (11) of equal width, which are comprised of, an elastic layer (12) and a plastic mesh (13) threaded together a long the perimeters (14), and two fastening connectors (15), each of which are made of a solid plastic plate (16), equipped with seven triangular eyelets (17) for receiving the tightening strings (18) and a Velcro® attached plastic mesh (19). Two narrow and long holes (20) are developed on the wider portion of each of the bands (11).

The elastic inner layers (12) of the bands (11) are made of the same soft elastic material, having a plurality of holes, as the elastic layer (6) of the back supporting frame (1). Velcro® is developed at the narrower end (21) of the inner sides of one band (11).

The outer layers of the bands (11) are made of plastic mesh (13) and Velcro®. Velcro®s are found on both of the narrow ends of the outer surfaces (22) of the bands (11), on both of the wider ends of the outer surfaces (23) of the bands (11), and along the horizontal center (24) of the outer surfaces of the bands (11). The fastening connectors (15) are attached to the Velcro® on both of the wider ends of the outer surfaces (23) of the bands (11).

FIG. 4 is a schematic diagram showing how to attach the back support frame (1) to the back supporting belt (10) and how to put the back support frame (1) on the patient's back. The back supporting frame (1) is attached to the belt (10) via two guiding nuts (25), fixed on the center of the exterior side of the inner-half of the rim of each solid plastic plate (2), guided through the two narrow and long holes (20) found on the wider portions of the belt, and held in place by two wide head bolts (26) which screw on to the nuts. This diagram demonstrates how a patient (27) places the supporting frame (1) and belt (10) around the waist, joins the Velcro® (21) and (24), and pulls the handles (28) of the fastening strings (18). When a patient (27) fastens the strings (18), the hinges (4) adjust according to the patients back shape and the two nuts (25) also adjust within the two narrow and long holes (20) found on the wider portions of the belt. Therefore, the distance between the two nuts (25) changes depending on the tightness of the fastening. These methods of adjustment enable the back supporting frame to conform to the specific shape of the individual patient's body (27) more than the previous arts, where the distance between the two nuts (25) (called guide projections in the prior arts) are fixed.

FIG. 5 is the schematic drawings showing the back supporting frames (1) worn by patients with varied waist contours. The distance (29) between the two plastic frames along the inner half of the rim vary, depending on the shape of the back of the individual patient (27), due to the combined movement of the two hinges (4) located on the upper and lower portions of the plates (2), and the position of the two guiding nuts (25) separately located on the center of the exterior side of the inner-half of the rim of each plastic plate (2), within the two narrow and long holes (20) found on the wider portions of the belt. In addition, the distance (29) between the two plastic frames along the vertical axis is adjustable, allowing the distance (29) between the two plates on the top portion to be different from the distance between the two plates on the bottom portion. This easily adjustable variation in the distance (29) between the two plastic frames enables patients with varied back contours and varied chest width to lower back width ratios to enjoy equal comfort and back support.

What is claimed is:

1. A waist support frame for a detachment type waist protecting belt to hold the vertebra region of a vertebra related patient is comprised of two plastic plates, each of which has a window at the center and one guiding nut on the center of the exterior side of the inner-half of the rim, connected by two hinges, which are attached to the upper and lower parts of the plastic plates, to form a saddle like shape that fits the contour of the waist of an individual patient.

2. The waist support frame in claim 1, wherein the distances between the two plastic plates along the inner half of the rim vary along the vertical axis, depending on the contour of the individual patients back, due to the combined movement of the two hinges and the two guiding nuts.

* * * * *